US008523565B2

(12) United States Patent
Matty et al.

(10) Patent No.: US 8,523,565 B2
(45) Date of Patent: *Sep. 3, 2013

(54) DENTAL APPLIANCE

(75) Inventors: Rick M. Matty, Scotts Valley, CA (US); Anthony W. Morefield, San Jose, CA (US); Devin K. Webb, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/466,874

(22) Filed: May 8, 2012

(65) Prior Publication Data
US 2012/0219922 A1 Aug. 30, 2012

Related U.S. Application Data

(62) Division of application No. 12/157,670, filed on Jun. 12, 2008, now Pat. No. 8,172,569.

(51) Int. Cl.
*A61C 7/08* (2006.01)
(52) U.S. Cl.
USPC ............. 433/24; 433/6; 433/80; 433/215
(58) Field of Classification Search
USPC ....... 433/6, 24, 34, 37, 80, 213–216; 700/98; 382/128; 128/861
See application file for complete search history.

(56) References Cited

U.S. PATENT DOCUMENTS

| 5,194,003 | A | 3/1993 | Garay et al. |
| 5,975,893 | A | 11/1999 | Chishti et al. |
| 6,471,970 | B1 | 10/2002 | Fanara et al. |
| 6,607,382 | B1 | 8/2003 | Kuo et al. |
| 6,626,669 | B2 | 9/2003 | Zegarelli |
| 6,984,128 | B2 | 1/2006 | Breining et al. |
| 7,328,706 | B2 * | 2/2008 | Bardach et al. ............ 128/861 |
| 2006/0115785 | A1 * | 6/2006 | Li et al. .................... 433/80 |
| 2011/0136072 | A1 * | 6/2011 | Li et al. .................... 433/18 |

FOREIGN PATENT DOCUMENTS

| WO | 2006/036597 | 4/2006 |
| WO | 2006/060547 | 6/2006 |

* cited by examiner

*Primary Examiner* — Cris L Rodriguez
*Assistant Examiner* — Edward Moran
(74) *Attorney, Agent, or Firm* — Brooks, Cameron & Huebsch, PLLC

(57) ABSTRACT

Embodiments include dental appliances, dental appliance systems, and methods of making and using such appliances. In one embodiment, a dental appliance includes a shell having a number of cavities to receive one or more teeth, each cavity having an inner surface. Fewer than all cavities are scaled-up in size by a first selected percentage over one or more dimensions of a corresponding tooth surface to provide a uniform space between the cavity inner surface and the corresponding tooth surface.

19 Claims, 6 Drawing Sheets

DENTAL APPLIANCE

PRIORITY INFORMATION

This application is a Divisional of U.S. application Ser. No. 12/157,670, filed Jun. 12, 2008, the entirety of which is incorporated herein by reference.

BACKGROUND

The present disclosure is related generally to the field of chemically treating individual teeth and/or associated gingival areas. More particularly, the present disclosure is related to chemically treating individual teeth and/or associated gingival areas during the course of dental alignment.

Repositioning teeth for aesthetic or other reasons has been accomplished by wearing what are commonly referred to as "braces." Braces typically encompass a variety of hardware such as brackets, archwires, ligatures, and O-rings. Attaching the hardware to a patient's teeth can be a tedious and time-consuming task requiring multiple meetings with a treatment professional.

Further, braces are attached to the surfaces of the teeth and since these surfaces are not exposed to food, drink, and other items while they are covered by the braces, oftentimes, the covered portion can have a different coloration when the braces are removed. This can be noticeable in some instances and since only a portion of the teeth is a different cooler, it can be difficult to remedy.

Moreover, from the patient's perspective, the use of braces can also be unsightly, uncomfortable, present a risk of infection, and can hinder effective brushing, flossing, and/or use of other dental hygiene procedures. Furthermore, in some instances, the use of braces can interfere with, or delay, other dental treatment of one or more teeth.

For example, application of whitening chemicals may not be effective while brackets are in place since the portion of tooth surface under the brackets can be left untreated, and thus be discolored with respect to the exposed tooth surface. Similarly, fluoride treatments may not reach the entire tooth structure.

DETAILED DESCRIPTION

Figures 1A, 1B:
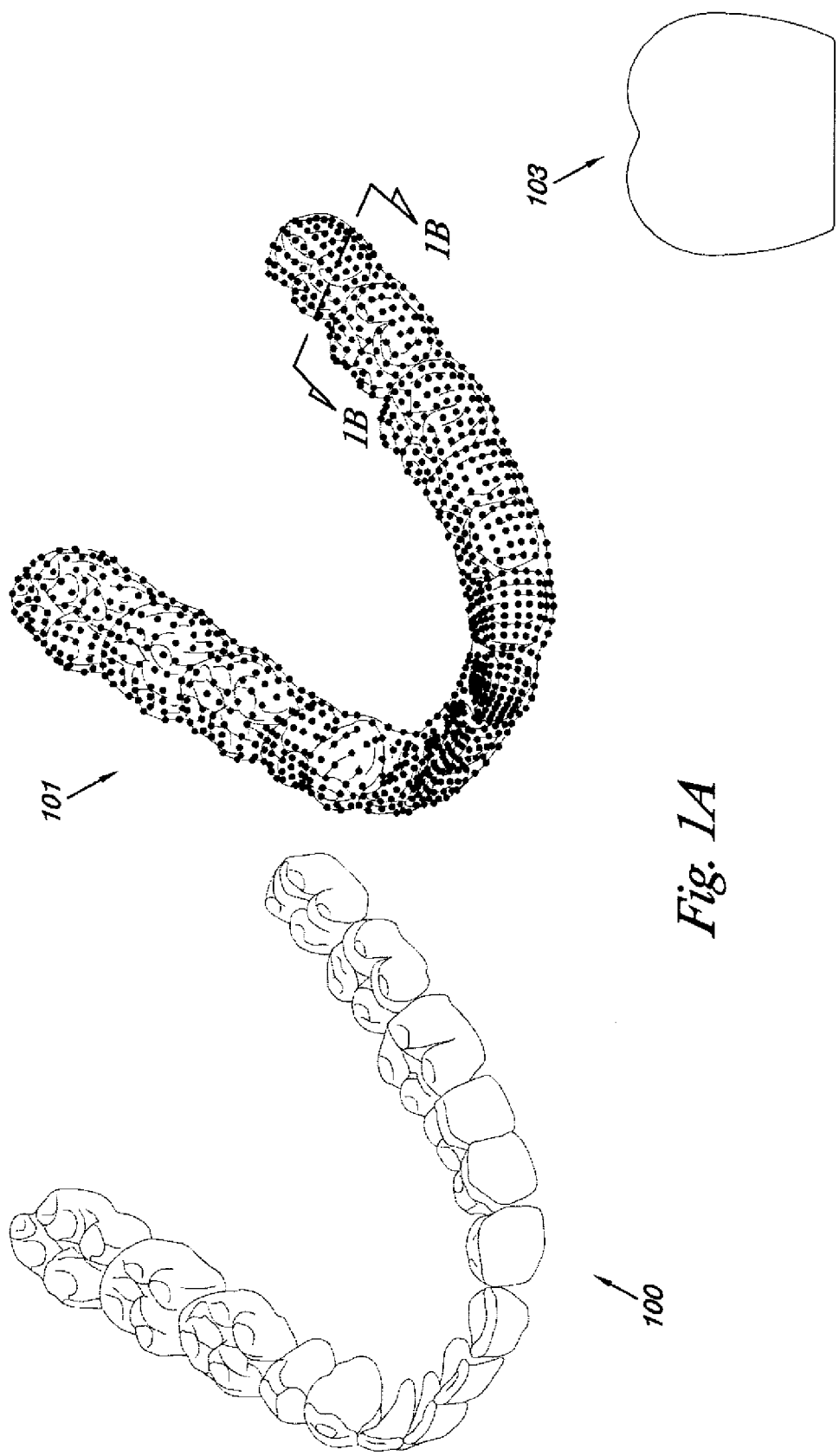
FIG. 1A illustrates an example of a patient's dentition and a digital representation of the patient's dentition that can be used to form a dental positioning appliance according to an embodiment of the present disclosure.
FIG. 1B illustrates an example of a cross section of the dentition that can be derived based on FIG. 1A (e.g., line 1B-1B), according to an embodiment of the present disclosure.

Embodiments of the present disclosure provide appliances, systems, and methods of making and using such appliances and/or systems. In various embodiments, a dental appliance, for example, can include a shell having a number of cavities to receive one or more teeth, each cavity having an inner surface. In some embodiments, fewer than all of the cavities are scaled-up in size by a first selected percentage over dimensions of a corresponding tooth surface to provide a uniform space between the cavity inner surface and the corresponding tooth surface.

Embodiments of the present disclosure are described in relation to the accompanying drawings, which will at least assist in illustrating the various features of the various embodiments. In the Figures, the first digit of a reference number refers to the Figure in which it is used, while the remaining two digits of the reference number refer to the same or equivalent parts of embodiment(s) of the present disclosure used throughout the several figures of the drawing. The scaling of the figures does not represent precise dimensions and/or dimensional ratios of the various elements illustrated herein.

Many dental treatments involve repositioning misaligned teeth and changing bite configurations for improved cosmetic appearance and dental function. Repositioning can be accomplished, for example, by applying controlled forces to one or more teeth over a period of time. Some dental processes use dental positioning appliances, rather than braces, for realigning teeth. Such appliances may, for example, utilize a thin shell of material having resilient properties, referred to as an "aligner" that generally conforms to a patient's teeth but is slightly out of alignment with the present (e.g., initial) tooth configuration.

Placement of such an appliance over the teeth provides controlled forces in specific locations to gradually move the teeth into a new configuration. Repetition of this process with successive appliances that provide progressive configurations eventually move the teeth through a series of intermediate arrangements to a final desired arrangement. An example of such a system is described in U.S. Pat. No. 5,975,893.

Such systems generally rely on designing and fabricating some, most, or all of the appliances, to be worn by the patient over time, at the outset of treatment. In some processes the design of the appliances relies on computer modeling of a series of successive tooth arrangements and the individual appliances are designed to be worn over the teeth and to reposition the teeth by using the appliances in a serial order, progressing from a first appliance, through each of the intermediate appliances, to the last appliance.

Appliances according to embodiments of the present disclosure may also be fabricated to conform to, or maintain, the present position of the patient's current dentition, and may, but do not have to, impart force to any of the teeth (e.g., for re-positioning). As such, the appliance may serve as a tray, or retainer, for delivery of material to one or more teeth without intended accompanying dental treatment functionality.

FIG. 1A illustrates an example of a patient's dentition and a digital representation of the patient's dentition that can be used to form a dental positioning appliance according to an embodiment of the present disclosure. In various embodiments, an impression of the patient's teeth 100 can be taken with various impression materials. The impression of the patient's teeth 100 can then be scanned and the data gathered by the scan can then be used to form a digital model of the impression of patient's teeth 101.

The digital model of the impression of the patient's teeth 101 can, for example, provide a digital image of the patient's teeth that maps the outside surface of the impression of the patient's teeth 100 to allow 360° viewing the patient's teeth. The patient's teeth can also be scanned directly to form the digital model.

The digital model 101 may be further determined from additional measurements of a patient's dentition. Surveying of the positioning of a patient's teeth within a mouth of a patient can, for example, be accomplished by manually taking a set of one or more data points by a treatment professional to determine gum line, or attachment point position, the data points then being entered into a computing device.

Data can also be obtained through an automated or semi-automated process. Further, a size and/or shape of an erupting tooth (teeth) can be estimated, for example, through use of a library of tooth sizes and/or shapes and/or information about the patient's other teeth. This information can be provided manually by a treatment professional or by an automated or semi-automated process in various embodiments.

Once obtained, the digital model 101 can then be studied by a treatment professional to determine if a dental condition exists with the patient's teeth. In some instances, the configuration of a patient's teeth can be studied easier and more thoroughly, for longer time periods, than can be achieved looking into the mouth of the patient while the patient is at the treatment professional office. The digital model 101 can also be used to fabricate a dental appliance corresponding to a present, anticipated, and/or desired configuration of the patient's dentition.

FIG. 1B illustrates an example of a cross section of the dentition that can be derived based on FIG. 1A (e.g., line 1B-1B), according to an embodiment of the present disclosure. In various embodiments, the digital model 101 of the impression of the patient's teeth can be viewed in cross section 103. This view can be beneficial to the treatment professional in evaluating the patient's teeth and diagnosing and forming a treatment plan for an orthodontic condition of the patient. The cross sectional view 103 of the digital model of the patient's teeth can provide a unique perspective of the patient's teeth that is not available through other processes, such as visual inspection or pictures of the patient's teeth.

A dental positioning appliance (e.g., an aligner) can be electronically derived from the digital model 101 of patient's teeth, and/or manipulations thereof, according to various embodiments of the present disclosure. A dental appliance includes multiple cavities for receiving one or more corresponding teeth.

A dental appliance generally conforms to a patient's teeth, but may be slightly out of alignment with respect to a given configuration of a patient's teeth. From the digital model 101, manipulations (e.g., movements) of individual teeth, or groups of teeth can be electronically modeled, such as by studying the effects of applying certain forces to various teeth. However, the dental appliance need not be out of alignment with a given configuration of the patient's teeth if not needed for treatment.

According to one or more embodiments of the present disclosure, a dental appliance such as an aligner, or tray, includes a number of cavities (e.g., cavity 204). The cavities generally correspond to one, but may correspond to multiple, individual teeth, and/or other features of a patient's dentition.

The dental appliance can be fabricated from a polymeric shell, or formed from some other material, and include a number of cavities shaped to receive corresponding teeth. The shell may be designed to fit over a number of, in many instances all teeth, present in the upper or lower jaw. Dental appliances can be configured to apply force to reposition one or more teeth from a first configuration of the teeth to a successive configuration of the teeth.

Various aspects of a digital model of a patient's teeth can be manipulated such as, for example, changing the size of individual teeth, or changing the size of a cavity corresponding to one or more particular teeth. One having ordinary skill in the art will appreciate that the size of a cavity of a dental appliance corresponding to a particular tooth may be changed by modifying the size of the particular tooth in the digital model of a patient's dentition, fabricating a physical model from the digital model by any number of manufacturing techniques, and subsequently forming a dental appliance from the physical model which includes the enlarged tooth.

In such embodiments, the size of a particular tooth may be changed by increasing one tooth dimension (e.g., length or girth), or several tooth dimensions simultaneously (e.g., length and girth). One methodology for uniformly increasing size of a particular tooth in the digital model is to scale-up selected tooth dimensions proportionately.

For example, some or all of the measured dimensions of a particular tooth may be uniformly increased in the digital model. Thus, a dental appliance formed from that digital model will result in a buffer, cushion or gap created around the particular tooth.

Tooth size modifications may be applied to one or more teeth simultaneously in some embodiments. When applied to multiple teeth simultaneously, the size modifications to individual teeth may be all the same, or selected to be different for one or more teeth.

The size of an individual tooth in a digital model, and/or the corresponding tooth cavity in a dental appliance formed from the digital model, may be modified from measured dimensions so as to be increased in size, or oversized, by a percentage of the original size, for example 1%, or by some other scaling factor.

Figure 2:
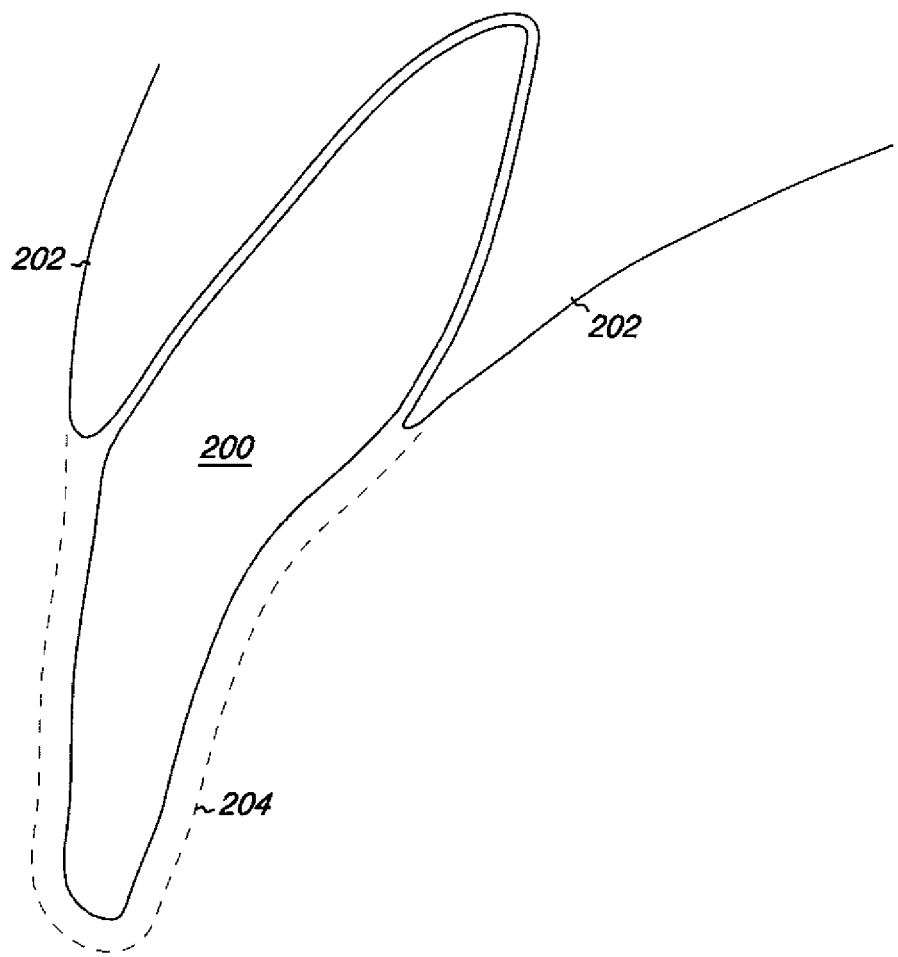
FIG. 2 illustrates an example of a scaled-up cavity of a dental appliance according to an embodiment of the present disclosure.

FIG. 2 illustrates an example of a scaled-up cavity 204 of a dental appliance according to an embodiment of the present disclosure. In the embodiment of FIG. 2, a tooth structure 200 is partially surrounded by a corresponding gingival margin area 202.

As discussed above, the tooth structure 200 has a particular shape and dimensions which can be accurately determined in three-dimensional space by a number of methods, including the impression and digital modeling techniques discussed with respect to FIGS. 1A and 1B. In the embodiment of FIG. 2, the cavity 204 of a dental appliance is shown fabricated to dimensions which are scaled-up from the dimensions of the corresponding tooth structure 200 so as to provide a uniform space surrounding the tooth structure 200, as shown in cross section in FIG. 2.

When referring to "scaling-up" portions of the digital model or the resulting shell/dental appliance, as used herein, the relative dimensions of portions of the model can be maintained. Thus, in scaling-up an individual tooth of the digital model, proportions of the tooth dimension are maintained relative to one another.

One skilled in the art will appreciate that a dental appliance fabricated based on a model having one or more oversized teeth will result in a shell possessing the same, or similar, qualities. Certain cavities in the shell can therefore be made larger than the corresponding actual tooth (teeth), thereby leaving a uniform space or gap between the actual tooth and the shell interior surfaces.

A uniform space surrounding a particular tooth, or teeth, may be bounded by the present position of other teeth. For example, in various embodiments, a particular tooth may be scaled-up into available empty space, but not into space occupied by adjacent teeth.

According to some embodiments of the present disclosure, a particular tooth can be scaled-up in the digital model (and thus in the corresponding dental appliance formed from such digital model) in directions other than toward adjacent teeth (e.g., in a buccal and/or lingual directions only). According to various embodiments, force can be applied through the dental appliance to move adjacent teeth away from space allotted to a scaled-up tooth, or teeth.

Embodiments of the present disclosure are not limited to an "aligner" that is intentionally fabricated slightly out of alignment with the present tooth configuration so as to provide force to one or more teeth. As will be appreciated by the reader, a dental appliance according to embodiments of the present disclosure may conform to a patient's tooth configuration. Thus, according to at least one embodiment of the present disclosure, a targeted tooth treatment and/or gingival treatment can be accomplished concurrent with alignment treatment, or separate and distinct from the alignment treatment.

Embodiments of the present disclosure include dental appliances, dental appliance systems, and methods of making and using such appliances and/or systems. In various embodiments, a dental appliance can include a shell having a number of cavities to receive one or more teeth, each cavity having an inner surface.

In some embodiments, one or more, but less than all, cavities can be scaled-up in size (e.g., by a first selected percentage) over dimensions of a corresponding tooth surface to provide a uniform space between the cavity inner surface and the corresponding tooth surface. The dental appliance may, or may not, be designed for application on moving force(s) to one or more teeth.

According to at least one embodiment of the present disclosure, a dental appliance adapted to fit the present configuration of a patient's teeth can include one or more cavities scaled-up in size to provide a space around one or more selected teeth for containing a chemical in contact with the one or more selected teeth. In such embodiments, at least one cavity corresponds in size to the measured dimensions of the corresponding one or more teeth, and serves as an anchor for the dental appliance to keep it located in a fixed orientation with respect to the teeth. Thus by having at least one such anchoring cavity snuggly fitted to one or more corresponding teeth, the spaces between one or more oversized cavities of the dental appliance and one or more corresponding teeth can be maintained with reduced or minimal relative movement in some instances.

The present disclosure also includes a number of method embodiments. For example, in some embodiments, a method can include forming a removable dental appliance, such as a positioning appliance, which includes identifying a first portion of a patient's dentition for chemical treatment, and digitally measuring dimensions of the patient's dentition.

A polymeric shell having a number of cavities shaped to receive the patient's teeth can be formed, with some of the cavities being sized to the measured dimensions. Cavities corresponding to the identified portion of the dentition are fabricated having at feast some dimensions larger than the measured dimensions to provide space between the dental positioning appliance and a corresponding tooth structure (e.g., one or more tooth surfaces of one or more teeth), the space adapted to contain a quantity of chemical in contact with a corresponding dentition.

The devices, methods, or systems of the present disclosure can employ any manner of positioners, trays, retainers, and/or other removable dental appliances for changing or maintaining teeth positions in connection with orthodontic treatment, or separate from orthodontic treatment. The systems for use in various embodiments of the present disclosure can utilize a single appliance solely for application of chemical treatment therapies, or a plurality of such appliances that can, for example, be worn by a patient successively in order to achieve the gradual tooth repositioning, as described herein.

In some embodiments, certain individual teeth, or small sets of the teeth, can be repositioned while others of the teeth provide a base or anchor region for holding the repositioning appliance in place as it applies a resilient repositioning force against the tooth or teeth to be repositioned. In such cases, one or more of the teeth which are moved can also serve as a base or anchor region for holding the repositioning appliance.

That is, the tooth and/or teeth cavities of the dental appliance which are being moved or re-positioned may serve as anchor teeth for cavities of the dental appliance which are formed oversized (e.g., by scaling-up) for chemically treating one or more certain teeth. In some embodiments, the gums and/or the palette can serve as an anchor region, thus allowing all or nearly all of the teeth to be repositioned and/or chemically treated using oversized cavities in the dental appliance at the same time, if desired.

The polymeric shell of the appliance may be a substantially transparent polymeric shell, for example, but embodiments of the present disclosure are not so limited. In some embodiments of the present disclosure, buccal portions of the shell cavities can be formed from a substantially transparent material. Other portions of the shell and/or cavities may, or may not, be substantially transparent, substantially opaque, and/or formed of an opaque material.

With respect to the embodiment of FIG. 2, the oversized cavity 204 can be fabricated for a particular tooth, chosen for example, as being in need of dental treatment such whitening of the tooth structure, application of fluoride, and/or some other condition which can be treated by a chemical application. The size of the cavity 204 can be scaled-up to a selected size according to embodiments of the present disclosure, the selection being to any of: a particular dimension(s), a particular scaling factor, to achieve particular gap or space characteristics, etc.

For example, one or more cavities of the appliance may be scaled-up to a first selected percentage in the range from 1% to 5% inclusive; however scaling up the appliance to the first selected percentage is not limited to this range. For example, the first selected percentage may be less than 1%, or more than 5% when desired to achieve a particular treatment effect, or accommodate a certain chemical or solution.

According to at least one embodiment of the present disclosure, cavity 204 is arranged to be scaled-up corresponding to only one side of a corresponding tooth surface, for example formed to leave a uniform space between the inner cavity wall and a corresponding tooth surface (such as the buccal surface), without being scaled-up to create a uniform space between the inner cavity wall and other corresponding tooth surfaces (such as the lingual surface).

In some embodiments, the one or more cavities being individually scaled-up to dimensions larger than the measured dimensions of the corresponding tooth may all be scaled-up to the same selected percentage, or may individually be scaled-up to an individually-selected percentage for each cavity, which may, or may not, be the same as a selected percentage for another cavity. As the reader will appreciate, some cavities may be scaled-up to provide a uniform space around a corresponding tooth, while the dimensions of other cavities are modified in ways other than scaling (e.g., increase in size along one dimension or by some fixed amount, etc.). In some embodiments, the tip of the tooth may have scaling different from that of other portions of the tooth, or the scaling may vary (e.g., taper) smaller or larger from the tip of the tooth toward the root.

According various embodiments, one or more cavities are sized to contain a chemical used to treat the corresponding tooth surface, such that the chemical remains in contact with the desired tooth surface. The one or more cavities can be appropriately sized, for example, to accommodate a chemical having a particular viscosity, to accommodate a particular quantity of chemical, and/or according to other properties of the material used to deliver the chemical and/or treatment considerations. For example, a selected percentage of a dental appliance cavity being scaled-up may be approximately 1%, or less, when being adapted for use with the chemical being fluoride, and a selected percentage of a dental appliance cavity being scaled-up may be approximately 5%, or more, when being adapted for use with the chemical being a whitening agent. The selected percentage may be different for the respective chemicals of the above-mentioned examples depending on the precise compound, or form, of the chemical delivery material (e.g., liquid, gel, powder, foam, etc.).

In general, appliance embodiments of the present disclosure have the one or more cavities scaled-up in size to have a uniform space between at least one inner cavity surface and the corresponding tooth surface. The corresponding tooth surface may be all of the exposed surfaces of a particular tooth, for example in the case of cavity prevention treatment, or the corresponding tooth surface may only be a buccal, or other, surface, for example in the case where the dental treatment is whitening.

Figure 3:
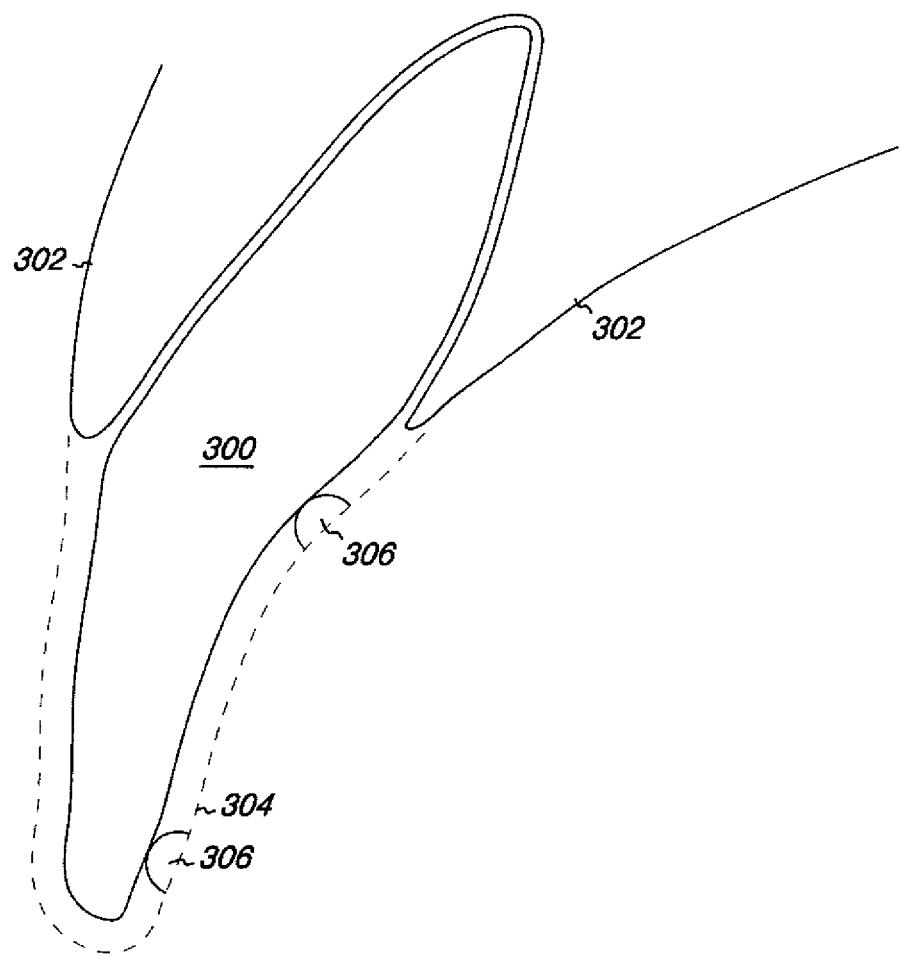
FIG. 3 illustrates another example of a scaled-up cavity of a dental appliance, the cavity having spacers, according to an embodiment of the present disclosure.

FIG. 3 illustrates an example of a scaled-up cavity of a dental appliance, the cavity having spacers, according to an embodiment of the present disclosure. In one or more embodiments of the present disclosure, such as that partially illustrated in FIG. 3, a system of removable dental positioning appliances includes a series of shells adapted to reposition one or more teeth from a first configuration to a successive configuration, each shall having a number of cavities to receive one or more teeth and each cavity having an inner surface.

One or more of the cavities are scaled-up in size by a selected percentage over dimensions of a corresponding tooth surface to provide a uniform space between the cavity inner surface and the corresponding tooth surface. The inner surface of the one or more cavities include spacers to offset the inner surface from the corresponding tooth surface. The reader will appreciate that such localized mechanical offsets, facilitate uniform distribution of chemical to the corresponding tooth surface area.

In the embodiment of FIG. 3, a tooth structure 300 is partially surrounded by a corresponding gingival area 302, and the cavity 304 of a dental appliance (e.g., shell) is scaled-up in the manner previously described above. A number of spacers 306 (e.g., one or more) protrude from the inner cavity surface toward the surface of the corresponding tooth 300. The spacers 306 extend for a distance above the inner cavity surface substantially equal to the gap, or uniform space, between the surface of the corresponding tooth 300 and inner surface of the cavity 304. One skilled in the art will appreciate that the spacers 306 thereby can provide a mechanical offset to maintain space between the surface of the corresponding tooth 300 and inner surface of the cavity 304, in some embodiments.

According to one or more embodiments of the present disclosure, one or more spacers 306 may be arranged to be in contact with at least one surface of the corresponding tooth surface (e.g., a lingual surface as shown in FIG. 3). According to at least one embodiment of the present disclosure, the number of spacers are arranged to be in contact with more than one surface of the corresponding tooth surface (e.g., a buccal surface as well as the lingual surface).

Embodiments of the present disclosure are not limited to any particular quantity, orientation, arrangement, or pattern of spacers 306. Spacers 306 may be of the same or different dimensions from one another (e.g., may be of differing heights above the inner surface of the cavity 304, or all extending a uniform dimension above the inner surface of the cavity 304).

Spacers 306 may be uniformly arranged in various dimensions, or located in specified locations. Some oversized cavities may include spacers, while others do not.

Spacers need not be of the rounded shape shown in FIG. 3, and may be formed as an offset at a particular point, or as a ridge or other geometry. The spacers need not be formed of additional material added to the inner surface of the cavity 304, but rather may be formed by molding the cavity wall to provide the offset (e.g., the outer cavity wall may have a corresponding indentation corresponding to a spacer structure.

In some embodiments, a resilient material can be used to form at least a portion of a spacer structure. In such embodiments, the spacer maybe shaped, or otherwise designed, to provide the same, or different, amounts of force (e.g., as the chemical material in the appliance is removed). One skilled in the art will appreciate the numerous ways that a physical offset may be fabricated as part of the dental appliance so as to provide a mechanical offset of a cavity inner wall from the corresponding tooth surface.

Figure 4:
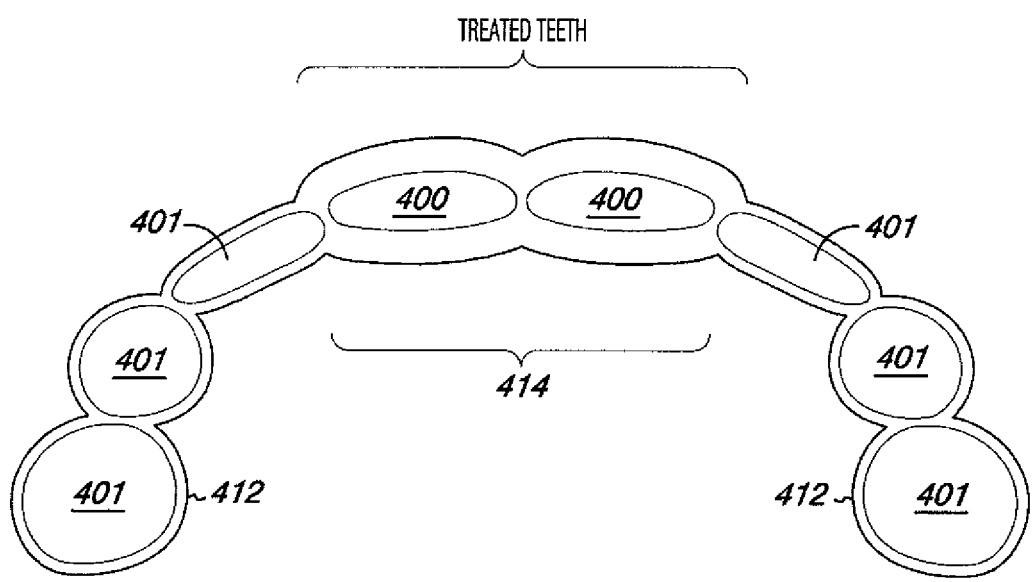
FIG. 4 illustrates an example of an appliance having one or more scaled-up cavities for selected teeth according to an embodiment of the present disclosure.

FIG. 4 illustrates an example of a dental appliance having one or more scaled-up cavities for selected teeth according to an embodiment of the present disclosure. FIG. 4 shows a top view of a patient's dentition fit into a dental appliance 404 according to one embodiment of the present disclosure. Illustrated are one or more treated teeth 400 positioned within one or more oversized (e.g., scaled-up) cavities 414 of the dental appliance 404, the treated teeth 400 having been selected for some form of chemical treatment. Other teeth 401 are not being selected to receive the aforementioned chemical treatment. The untreated teeth 401 are shown positioned within more fitted (e.g., not scaled-up) cavities 412 of the dental appliance 404.

The reader will appreciate the dental appliance 404 is configured such that more space is left between the treated teeth 400 selected for chemical treatment and the corresponding oversized cavity 414 of the dental appliance, than the space, if any, between untreated teeth 401 (e.g., not presently being chemically treated) and a corresponding fitted cavity 412 of the dental appliance 404. One skilled in the art will appreciate that the close fitting cavities 412 of the dental appliance 404 hold the dental appliance 404 in a fixed position with respect to the patient's dentition, such that the oversized cavities 414 of the dental appliance 404 are held in relative place around the treated teeth 400. In this manner, a chemical placed within an oversized cavity 414 is kept in contact with the treated teeth 400.

One or more teeth may be treated at one time. The treated teeth may (as is shown in FIG. 4), but need not be, adjacent one another. The oversized cavities may also be used to relieve pressure on one or more teeth, and thus the space left around a particular tooth need not be filled with a chemical in employing the dental appliance of the present disclosure.

One skilled in the art will also appreciate that some or all teeth may be treated simultaneously, with the dental appliance formed to allow more space around certain teeth than others. For example, it may be advantageous to fabricate a dental appliance having additional fluid capacity surrounding the two front teeth than around the remaining teeth, such as for whitening applications intended to target selected teeth more vigorously than others.

Figure 5:
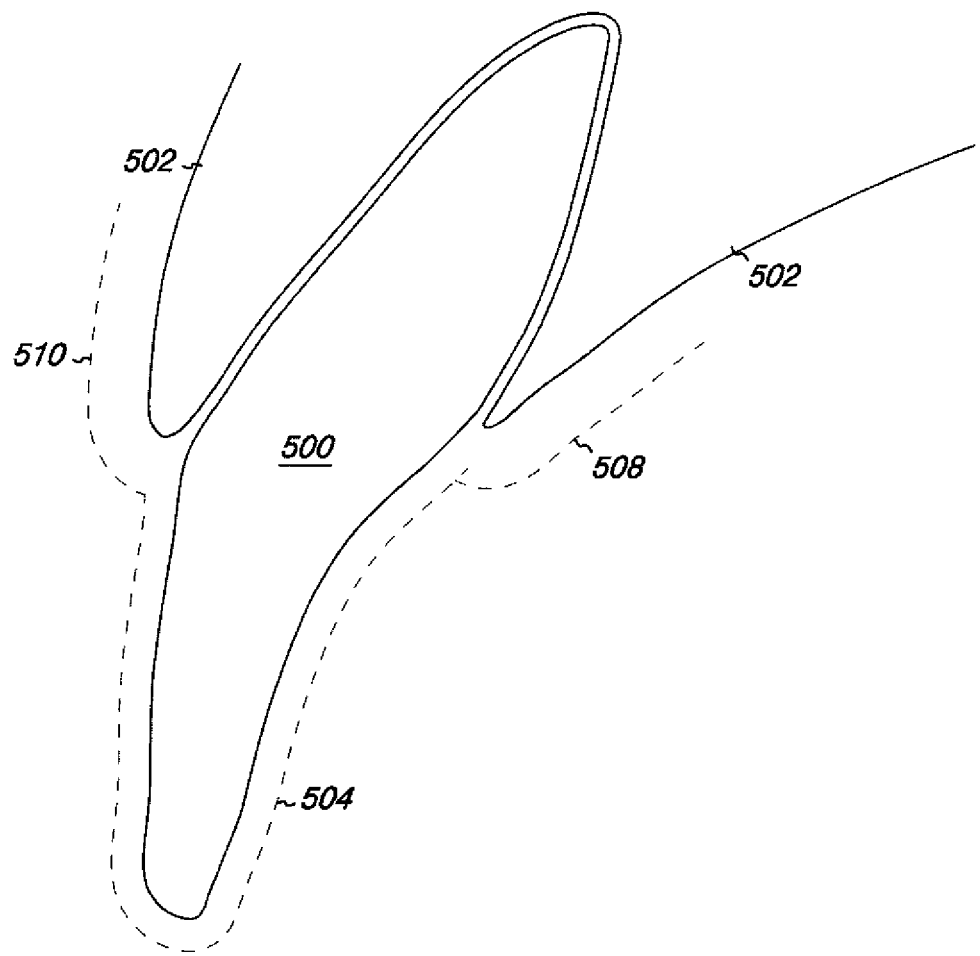
FIG. 5 illustrates an example of a scaled-up cavity of an appliance, including a pocket surrounding the gingiva, according to an embodiment of the present disclosure.

FIG. 5 illustrates an example of a scaled-up cavity of an appliance, including a pocket surrounding the gingiva, according to an embodiment of the present disclosure. As shown in FIG. 5, a tooth structure 500 is partially surrounded by a corresponding gingival margin area 502.

The exposed tooth structure can be enclosed by an oversized (e.g., scaled-up) dental appliance cavity 504, which can be a portion of a shell as previously described above. According to various embodiments of the present disclosure, the cavity walls of the shell may extend up and over a corresponding gingival margin area 502 outer surface.

In a manner similar to the dental appliance cavity 504 surrounding the tooth surface, the shell may be fabricated to allow for a space between the upper walls of a particular cavity, or the shell, and the corresponding gingival margin area 502, so as to form a lingual pocket 508 and/or a buccal pocket 510 adapted to hold a chemical adjacent the corresponding gingival margin area 502. In this manner, the dental appliance can be used to chemically treat selected areas of the gingival margin area 502. According to at least one embodiment of the present disclosure, the lingual pocket 508 and/or buccal pocket 510 areas can be contiguous with cavity 504.

Like the tooth structure itself, measurements with respect to the gingival margin area 502 can be made by a variety of methods such as were discussed above with respect to measurements of the teeth. The gingival regions can then be included in the digital model and/or subsequent physical models produced therefrom, with the dimensions thereof being manipulated in a manner similar to that described with regard to the tooth surface. Therefore, a dental appliance can be scaled-up from the measured dental and gingival surfaces uniformly by a selected percentage, for example, or by some other dimensional increase methodology to provide a uniform space between the gingival and dental appliance.

The amount by which a cavity is scaled-up from the corresponding gingival margin area 502 measurements may be the same, or different, than the quantity used to scale-up the cavity with respect to a corresponding tooth structure. Scaling-up the dental appliance dimensions with respect to corresponding gingival margin area 502 measurements provides a uniform space therebetween. Such uniform space can be arranged and adapted to hold a reservoir of material in contact with the gingival outer surface to treat periodontal conditions, such as gel, paste, foam, liquid, or powder.

According to one or more embodiments of the present disclosure, a lingual pocket 508 and/or a buccal pocket 510 may be formed independently from any cavity 504 associated with a particular tooth. For example, a lingual pocket 508 and/or a buccal pocket 510 may be formed for a tooth being used as an anchor for the dental appliance with a snug-fitting cavity for receiving the tooth structure.

In some embodiments, the cavity 504 and one or more portions of the lingual and/or buccal pockets 508 and 510 can be sized to fit snugly against the tooth/gingival surface to which they are adjacent. In such embodiments, the tight fit can be used to hold the appliance in place and/or to isolate a particular portion of the tooth and/or gingiva.

For example, in some embodiments, the upper portion or both the lingual and buccal pockets 508 and 510 can be sized to fit snugly against the gingival surface to which they are adjacent. The cavity 504 can also be sized to fit snugly.

In such an embodiment, the lower portions of both the lingual and buccal pockets 508 and 510 can provide a more loose fitting area into which a material may be placed for localized treatment of the lower gingiva (e.g., the gingival margin) and/or the interface between the gingiva 502 and the tooth 500. Such embodiments may, for instance, be used where the treatment material (e.g., chemical solution) is to be concentrated on the area for a period of time without it seeping into the mouth of the patient. Such embodiments may also be aided by having the cavity 504 fit snugly such that little fluid movement is possible into the cavity from the looser portions of the pockets 508 and/or 510.

Thus, embodiments of the present disclosure may be configured to only provide periodontal chemical treatment, with or without orthodontic treatment features, and with or without, oversized cavities for chemical treatment of tooth structure. Embodiments of the present disclosure contemplate any combination of these features, alone or in combination with one another.

With regard to the chemicals which might be utilized with the devices, systems, and methods of the present disclosure, oral health concerns often include tooth decay, gingivitis, and periodontitis, to name a few. Tooth decay, for example, may be largely prevented or arrested with fluoride treatment. Treatment materials can include toothpastes, gels, rinses and varnishes.

Gum disease, such as gingivitis or periodontitis, can be caused by bacterial growth associated with dental plaque and calculus deposits. Bacterial growth can be reduced or prevented by mechanically removing the plaque from the tooth surfaces.

However, chronic gingivitis and tooth decay have plagued many individuals who in fact comply with good oral hygiene methods and plaque removal. This may be due to a variety of factors including genetic predispositions, illnesses, mouth breathing, and medical treatment programs, among other causes. In such cases, bacterial control may be accomplished with the use of antibacterial drugs, or other prevention materials.

An antibacterial agent that may be effective in reducing the activity of many strains of oral flora is chlorhexidine. Chlorhexidine is a cationic biguanide microbicide with a broad spectrum of activity against many forms of bacteria and fungi. Therefore, it has been a popular agent in many studies of gingivitis reversal.

Chlorhexidine can be delivered to the oral environment through the use of oral rinses. These rinses provide short term application of the material. However, sustained delivery to the gingiva can be accomplished with the use of dental appliances according to embodiments of the present disclosure.

Another antibacterial agent is tetracycline. Tetracycline is a broad spectrum antibiotic which may be effective against many groups of pathogenic bacteria, both gram positive and negative.

Tetracycline may be combined with an antifungal agent, such as amphotericin, to provide activity against fungi. Tetracycline may be traditionally been delivered to the oral environment through systemic administration, although localized delivery can be accomplished using the dental appliances of the present disclosure. In addition, a number of other antibacterial drugs are available for dental and periodontal therapy, and may be administered locally using one or more of the dental appliances according to the present disclosure, formed to leave uniform, or non-uniform, space between the dental appliance and a tooth surface or teeth surfaces at the targeted point of chemical application.

Cosmetic treatments often include tooth bleaching or whitening and breath-freshening products. Discolorations of enamel and dentin may occur, for example, due to aging, consumption of staining substances (e.g., coffee, tea, colas, and tobacco), trauma, staining due to systemic tetracycline (antibiotic) therapy, excessive fluoride, nerve degeneration, and old dental restorations, among other causes.

Bleaching lightens these discolorations for a whiter or brighter appearance. A bleaching gel can be provided in the selected oversized cavities of a dental appliance according to the present disclosure. The dental appliance fits over the teeth, and can be worn at night, or during the day. Breath freshening products are often used by patients to treat halitosis or for enjoyment of the taste. These include a variety of sprays, rinses, mints, gums, or candies, to name a few. Such breath freshening products can be provided (e.g., formed in or placed) in the dental appliance of the present disclosure.

Many of these therapies utilize access to the teeth and gingival margin which are typically covered by the repositioning appliance when in use. In addition, some of these therapies may best be administered by localized delivery over extended periods of time which could otherwise create substantial interruption of a treatment plan.

For example, low level delivery of antibiotics by sustained release methods is often desired to treat periodontal disease. Likewise, treatments such as bleaching and whitening may create an interruption of the treatment plan for up to two weeks. Removal of the appliance during these periods would lengthen the overall treatment period.

In addition, many of these therapies utilize the usage of specific devices, gels, rinses, applicators and instructions for each administration of therapy. These accessories may be costly, bulky, and difficult to use.

Although removal of the appliance during treatment should be minimized, it may be necessary to remove the appliance during daily oral hygiene routines, such as brushing and flossing of the teeth. Likewise, the appliance may be removed from time to time for participation in athletic activities or for comfort, such as when eating.

Figure 6:
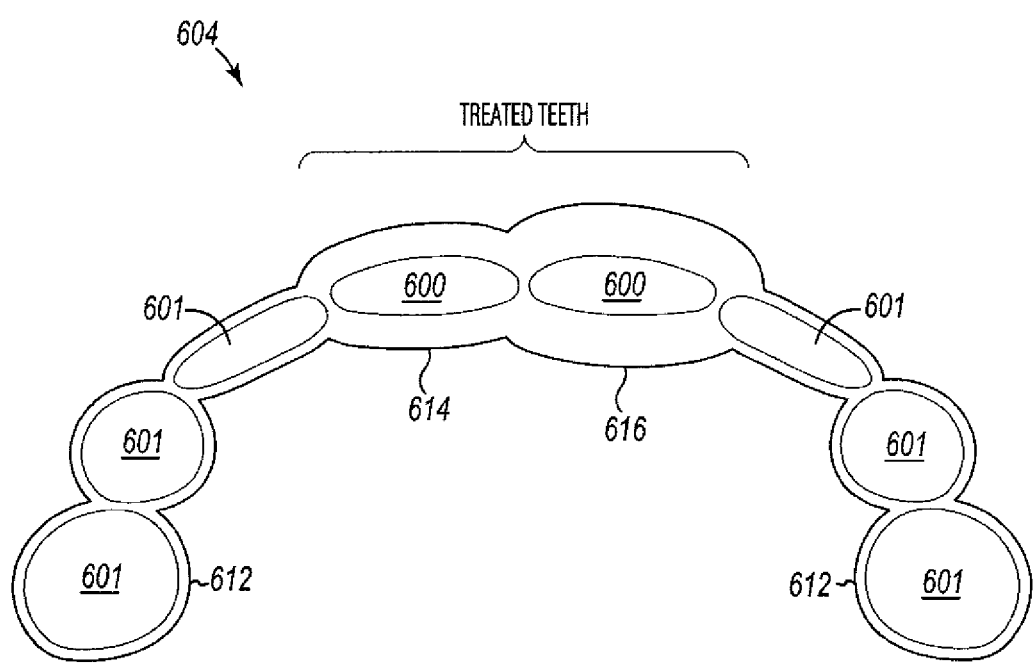
FIG. 6 illustrates an example of an appliance having one or more scaled-up cavities for selected teeth according to an embodiment of the present disclosure.

FIG. 6 illustrates an example of a dental appliance having one or more scaled-up cavities for selected teeth according to an embodiment of the present disclosure. FIG. 6 shows a top view of a patient's dentition fit into a dental appliance 604 according to one embodiment of the present disclosure. Illustrated are one or more treated teeth 600 positioned within one or more cavities 614 scaled-up in size by a first percentage and one or more cavities 616 scaled-up in size by a second percentage, the treated teeth 600 having been selected for some form of chemical treatment. Other teeth 601 are not being selected to receive the aforementioned chemical treatment. The untreated teeth 601 are shown positioned within more fitted (e.g., not scaled-up) cavities 612 of the dental appliance 604.

According to various embodiments of the present disclosure, a dental appliance can be fabricated to provide space over an area associated with an erupting tooth which is covered by the gingiva on the jaw, for example, to reduce mechanical irritation of the area associated with physical contact of the dental appliance with the gingival. Such embodiments may permit containment of a chemical to the area, such as a pain or inflammation medication, in some instances.

In various embodiments, a computing system can be used in the design of dental appliances thereof that can be used in association with the fabrication of embodiments of the present disclosure. Such a computing system may include one or more computing devices having, for example, a processor and memory. The memory can include various types of information including data (e.g., dentition measurement, and/or digital model data) and/or executable instructions to perform the methods discussed herein.

Some embodiments can include a network interface. Such an interface can allow, for example, for processing on another networked computing device. Such devices can be used to obtain information about the patient or executable instructions for use with various embodiments provided herein, in some instances.

Various embodiments can include one or more input and/or output interfaces. Such interfaces can be used, for instance, to connect the computing device with one or more input or output devices. For example, a system may include connectivity to a scanning device, a camera dock, a keyboard, and/or other peripherals.

Such connectivity can allow for the input of image information (e.g., scanned images and/or digital pictures, etc.), and instructions (e.g., input via keyboard), among other types of information. Although some embodiments may be distributed among various computing devices within one or more networks, such systems can be beneficial in allowing for the capture, calculation, and/or analysis of the various information discussed herein.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method of forming a removable dental positioning appliance, the method comprising:

digitally measuring dimensions of the patient's dentition;

forming a polymeric shell having a number of cavities shaped to receive the patient's dentition, at least one of the cavities being sized snuggly based on the measured dimensions;

fabricating fewer than all of the number of cavities corresponding to the dentition that are larger than the measured dimensions by a first percentage to provide space adapted to contain a quantity of chemical in contact with the dentition; and fabricating at least one of the number of cavities scaled-up in size by a second percentage that is different than the first percentage.

2. The method of claim 1, where the polymeric shell is shaped to reposition one or more teeth from a first orientation to a successive orientation.

3. The method of claim 1, where a portion of the number of cavities are scaled-up in size by a selectable percentage from the digitally measured dimensions to provide a space between an inner surface of the cavity and a corresponding tooth surface.

4. The method of claim 1, where the method includes offsetting the inner surface of the scaled-up cavities from a corresponding tooth surface using spacer structures formed into the polymeric shell.

5. The method of claim 1, where the portion of the cavities extend around a gingival margin area supporting a corresponding tooth surface so as to form a pocket of space between the inner surface of the cavity and the corresponding gingival margin area.

6. A method of forming a removable dental positioning appliance, the method comprising:

forming a shell having a number of cavities to receive one or more teeth, each cavity having an inner surface, where forming the shell includes:

forming fewer than all of the number of cavities scaled-up in size by a first percentage over one or more dimensions of a corresponding tooth surface to provide a space between the cavity inner surface and the corresponding tooth surface for containment of a chemical to treat the corresponding tooth surface; and forming at least one of the number of cavities scaled-up in size by a second percentage that is different than the first percentage;

where the inner surface of the cavities that are scaled-up in size have scaled-up proportions of the dimensions relative to the corresponding tooth surface; and where the first percentage is based on one or more properties of the chemical used to treat the corresponding tooth surface.

7. The method of claim 6, where forming the shell includes arranging the number of cavities to reposition the one or more teeth from a first configuration to a successive configuration.

8. The method of claim 6, where forming the shell comprises forming a polymeric shell.

9. The method of claim 8, where forming the shell comprises forming buccal portions of the cavities of a transparent polymeric material.

10. The method of claim 6, where the one or more properties of the chemical includes a particular viscosity of the chemical, a particular quantity of the chemical, and a particular form of delivery of the chemical.

11. The method of claim 10, where forming fewer than all of the number of cavities scaled-up in size by a first percentage comprises forming cavities scaled-up in size by the first percentage sized to contain fluoride to treat the corresponding tooth surface, the first percentage being within a range of 1% to 0%.

12. The method of claim 10, where forming fewer than all of the number of cavities scaled-up in size by a first percentage comprises forming cavities sized to contain a whitening agent to treat the corresponding tooth surface, the first percentage being 5%.

13. The method of claim 6, where the corresponding tooth surface comprises a buccal surface.

14. The method of claim 6, where the corresponding tooth surface includes all accessible surfaces of the corresponding tooth.

15. The method of claim 6, where forming the shell includes forming a number of spacers that protrude from the inner cavity surface toward the corresponding tooth surface for a distance substantially equal to the space.

16. The method of claim 6, where forming the shell includes forming a portion of at least one cavity that extends over a corresponding gingival outer surface adjacent the corresponding tooth surface to create a second space between a cavity inner surface and the corresponding gingival outer surface, the second space being contiguous with the first space.

17. The method of claim 16, where forming the portion of the at least one cavity extending over the corresponding gingival outer surface comprises forming the portion of the at least one cavity scaled-up in size by a third percentage over dimensions of the corresponding gingival outer surface.

18. The method of claim 16, where forming the shell includes arranging the second space to hold a reservoir of material in contact with the corresponding gingival outer surface to treat periodontal conditions.

19. The method of claim 18, where forming the shell includes arranging the second space to hold material selected from the group including: gel, paste, foam, liquid, and powder.

* * * * *